(12) United States Patent
    Robinson

(10) Patent No.: US 10,076,595 B2
(45) Date of Patent: *Sep. 18, 2018

(54) SYSTEMS AND METHODS FOR BLOOD RECOVERY FROM ABSORBENT SURGICAL MATERIALS

(71) Applicant: Cyclone Medtech, Inc., St. Paul, MN (US)

(72) Inventor: Len Robinson, Brooklyn Park, MN (US)

(73) Assignee: Cyclone Medtech, Inc., St. Paul, MN (US)

( * ) Notice: Subject to any disclaimer, the term of this patent is extended or adjusted under 35 U.S.C. 154(b) by 156 days.

This patent is subject to a terminal disclaimer.

(21) Appl. No.: 14/533,711

(22) Filed: Nov. 5, 2014

(65) Prior Publication Data

US 2015/0059813 A1 Mar. 5, 2015

Related U.S. Application Data

(62) Division of application No. 13/966,906, filed on Aug. 14, 2013, now abandoned.

(60) Provisional application No. 61/683,315, filed on Aug. 15, 2012.

(51) Int. Cl.
| | |
|---|---|
| *A61M 1/02* | (2006.01) |
| *B08B 3/06* | (2006.01) |
| *B08B 3/04* | (2006.01) |
| *B30B 9/04* | (2006.01) |

(Continued)

(52) U.S. Cl.
CPC ............ *A61M 1/0281* (2013.01); *B08B 3/04* (2013.01); *B08B 3/06* (2013.01); *B08B 3/08* (2013.01); *B30B 9/04* (2013.01); *D06F 23/04* (2013.01)

(58) Field of Classification Search
CPC . D06F 21/08; D06F 23/04; B08B 3/06; B08B 3/08; A61M 1/0281
See application file for complete search history.

(56) References Cited

U.S. PATENT DOCUMENTS 1,474,277 A * 11/1923 Martel .................... D06F 17/04
                                                    134/182
1,886,578 A    11/1932 Pedrazzo
(Continued)

FOREIGN PATENT DOCUMENTS

| CN | 2602043 Y | 12/2002 |
|---|---|---|
| CN | 2804152 Y * | 8/2006 |

(Continued)

OTHER PUBLICATIONS

Machine translation of CN 2804152 Y, dated Aug. 2006.*

(Continued)

*Primary Examiner* — Joseph L. Perrin
*Assistant Examiner* — Kevin G Lee
(74) *Attorney, Agent, or Firm* — Kinney & Lange, P.A.

(57) ABSTRACT

Systems and methods are described for salvaging red blood cells from patients during a surgical procedure. In one general aspect, a system is described for extracting blood from blood-soaked absorbent surgical materials such as surgical sponges, gauze, tape, and the like. The collected blood and fluids from these materials can be transferred to a cell salvage machine for harvesting viable red blood cells for autotransfusion.

7 Claims, 5 Drawing Sheets

(51) Int. Cl.
  *B08B 3/08* (2006.01)
  *D06F 23/04* (2006.01)

(56) References Cited

U.S. PATENT DOCUMENTS

| | | | |
|---|---|---|---|
| 2,672,744 A * | 3/1954 | Kirby | D06F 23/04 |
| | | | 68/152 |
| 3,706,412 A | 12/1972 | Latham, Jr. | |
| 3,749,285 A | 7/1973 | Latham, Jr. | |
| 3,768,653 A | 10/1973 | Brumfield | |
| 3,785,549 A | 1/1974 | Latham, Jr. | |
| 3,831,813 A | 8/1974 | Latham, Jr. | |
| 3,916,892 A | 11/1975 | Latham, Jr. | |
| 3,965,896 A | 6/1976 | Swank | |
| 4,033,345 A | 7/1977 | Sorenson et al. | |
| 4,054,523 A | 10/1977 | Ingenito et al. | |
| 4,059,108 A | 11/1977 | Latham, Jr. | |
| 4,086,924 A | 5/1978 | Latham, Jr. | |
| 4,115,277 A | 9/1978 | Swank | |
| 4,204,537 A | 5/1980 | Latham, Jr. | |
| 4,243,531 A | 1/1981 | Crockett et al. | |
| 4,285,464 A | 8/1981 | Latham, Jr. | |
| 4,300,717 A | 11/1981 | Latham, Jr. | |
| 4,303,193 A | 12/1981 | Latham, Jr. | |
| 4,304,357 A | 12/1981 | Schoendorfer | |
| 4,381,776 A | 5/1983 | Latham, Jr. | |
| 4,385,630 A | 5/1983 | Gilcher et al. | |
| 4,402,680 A | 9/1983 | Schoendorfer | |
| 4,405,079 A | 9/1983 | Schoendorfer | |
| 4,416,654 A | 11/1983 | Schoendorfer et al. | |
| 4,417,884 A | 11/1983 | Schoendorfer et al. | |
| 4,421,506 A | 12/1983 | Danby et al. | |
| 4,425,114 A | 1/1984 | Schoendorfer et al. | |
| 4,445,883 A | 5/1984 | Schoendorfer | |
| 4,464,167 A | 8/1984 | Schoendorfer et al. | |
| 4,466,888 A | 8/1984 | Verkaart | |
| 4,474,568 A | 10/1984 | Schoendorfer et al. | |
| 4,480,751 A | 11/1984 | Lueptow | |
| 4,482,342 A | 11/1984 | Lueptow | |
| 4,531,954 A | 7/1985 | Klein | |
| 4,561,868 A | 12/1985 | von Reis et al. | |
| 4,673,423 A | 6/1987 | Yumlu | |
| 4,681,677 A | 7/1987 | Kuh et al. | |
| 4,704,203 A | 11/1987 | Reed | |
| 4,740,202 A | 4/1988 | Stacey et al. | |
| 4,743,371 A | 5/1988 | Servas et al. | |
| 4,755,300 A | 7/1988 | Fischel et al. | |
| 4,758,337 A | 7/1988 | Kohn et al. | |
| 4,767,396 A | 8/1988 | Powers | |
| 4,795,448 A | 1/1989 | Stacey et al. | |
| 4,808,307 A | 2/1989 | Fischel et al. | |
| 4,871,453 A | 10/1989 | Kumar | |
| 4,886,487 A | 12/1989 | Solem et al. | |
| 4,889,524 A | 12/1989 | Fell et al. | |
| 4,898,572 A | 2/1990 | Surugue nee Lasnier et al. | |
| 4,943,273 A | 7/1990 | Pages | |
| 4,954,251 A | 9/1990 | Barnes et al. | |
| D312,128 S | 11/1990 | Headley | |
| 4,983,158 A | 1/1991 | Headley | |
| 5,015,388 A | 5/1991 | Pusineri et al. | |
| 5,045,048 A | 9/1991 | Kaleskas et al. | |
| 5,055,198 A | 10/1991 | Shettigar | |
| 5,100,372 A | 3/1992 | Headley | |
| 5,133,703 A | 7/1992 | Boehringer et al. | |
| 5,135,645 A | 8/1992 | Sklenak et al. | |
| 5,149,318 A | 9/1992 | Lindsay | |
| 5,183,569 A | 2/1993 | Kyriacou | |
| 5,215,519 A | 6/1993 | Shettigar | |
| 5,223,154 A | 6/1993 | MacPherson, Jr. et al. | |
| 5,273,517 A | 12/1993 | Barone et al. | |
| 5,304,164 A | 4/1994 | Lindsay | |
| 5,311,908 A | 5/1994 | Barone et al. | |
| 5,348,533 A | 9/1994 | Papillon et al. | |
| 5,387,088 A | 2/1995 | Knapp et al. | |
| 5,387,187 A | 2/1995 | Fell et al. | |
| 5,399,156 A | 3/1995 | Lindsay | |
| 5,405,308 A | 4/1995 | Headley et al. | |
| 5,411,705 A | 5/1995 | Thor et al. | |
| 5,423,738 A | 6/1995 | Robinson et al. | |
| 5,458,459 A | 10/1995 | Hubbard et al. | |
| 5,458,566 A | 10/1995 | Herrig et al. | |
| 5,478,479 A | 12/1995 | Herrig | |
| 5,494,592 A | 2/1996 | Latham, Jr. et al. | |
| 5,505,683 A | 4/1996 | Geringer et al. | |
| 5,514,070 A | 5/1996 | Pages | |
| 5,514,095 A | 5/1996 | Brightbill et al. | |
| D377,685 S | 1/1997 | Sibinga et al. | |
| 5,607,579 A | 3/1997 | Latham, Jr. et al. | |
| 5,634,893 A | 6/1997 | Rishton | |
| 5,637,082 A | 6/1997 | Pages et al. | |
| 5,643,193 A | 7/1997 | Papillon et al. | |
| 5,658,231 A | 8/1997 | Schmitt et al. | |
| 5,674,173 A | 10/1997 | Hlavinka et al. | |
| 5,681,709 A | 10/1997 | Mochnal et al. | |
| 5,725,777 A | 3/1998 | Taylor | |
| 5,769,811 A | 6/1998 | Stacey et al. | |
| 5,770,073 A | 6/1998 | Bach et al. | |
| 5,783,093 A | 7/1998 | Holme | |
| 5,791,592 A | 8/1998 | Nolan et al. | |
| 5,800,721 A | 9/1998 | McBride | |
| 5,879,624 A | 3/1999 | Boehringer et al. | |
| 5,882,289 A | 3/1999 | Sakota et al. | |
| 5,954,971 A | 9/1999 | Pages et al. | |
| 5,971,948 A | 10/1999 | Pages et al. | |
| 6,026,684 A | 2/2000 | Calder | |
| D423,095 S | 4/2000 | Gilcher et al. | |
| 6,099,493 A | 8/2000 | Swisher | |
| 6,113,554 A | 9/2000 | Gilcher et al. | |
| 6,130,264 A * | 10/2000 | Cercone | B08B 3/08 |
| | | | 521/50 |
| 6,193,681 B1 | 2/2001 | Davidner et al. | |
| 6,250,331 B1 | 6/2001 | Nardi | |
| 6,251,291 B1 | 6/2001 | Lamphere et al. | |
| 6,267,925 B1 | 7/2001 | Pages | |
| 6,402,702 B1 | 6/2002 | Gilcher et al. | |
| 6,440,372 B1 | 8/2002 | Pages | |
| 6,464,624 B2 | 10/2002 | Pages | |
| 6,558,307 B2 | 5/2003 | Headley | |
| 6,558,341 B1 | 5/2003 | Swisher | |
| 6,602,179 B1 | 8/2003 | Headley et al. | |
| 6,629,919 B2 | 10/2003 | Egozy et al. | |
| 6,632,191 B1 | 10/2003 | Headley et al. | |
| 6,641,552 B1 | 11/2003 | Kingsley et al. | |
| 6,705,983 B1 | 3/2004 | Rochat | |
| 6,709,377 B1 | 3/2004 | Rochat | |
| 6,824,506 B1 | 11/2004 | Lamphere et al. | |
| 6,878,545 B2 | 4/2005 | Deckwer et al. | |
| 6,964,646 B1 | 11/2005 | Biesel | |
| 7,055,401 B2 | 6/2006 | Prybella et al. | |
| 7,063,816 B2 | 6/2006 | Maianti et al. | |
| RE39,449 E | 12/2006 | Pages | |
| 7,332,125 B2 | 2/2008 | Cianci et al. | |
| 7,452,322 B2 | 11/2008 | Headley et al. | |
| 7,601,268 B2 | 10/2009 | Ragusa | |
| D609,334 S | 2/2010 | Cameron et al. | |
| D632,792 S | 2/2011 | Cameron et al. | |
| 8,105,422 B2 | 1/2012 | Betting et al. | |
| 8,157,103 B2 | 4/2012 | Eagle et al. | |
| 8,157,775 B2 | 4/2012 | Bobroff et al. | |
| 8,157,792 B2 | 4/2012 | Dolliver et al. | |
| 2006/0282109 A1 | 12/2006 | Jansen et al. | |
| 2008/0141732 A1* | 6/2008 | Leidig | D06F 37/14 |
| | | | 68/13 R |
| 2009/0259161 A1 | 10/2009 | Ghelli et al. | |
| 2010/0234788 A1 | 9/2010 | Pages et al. | |
| 2010/0236012 A1 | 9/2010 | Horne | |
| 2010/0292628 A1 | 11/2010 | Powers et al. | |
| 2011/0026009 A1 | 2/2011 | Knutson et al. | |
| 2011/0068061 A1 | 3/2011 | Eagle et al. | |
| 2011/0178453 A1 | 7/2011 | Pages et al. | |
| 2011/0281346 A1 | 11/2011 | Halpern et al. | |
| 2012/0165642 A1 | 6/2012 | Krensky et al. | |
| 2012/0168377 A1 | 7/2012 | Eagle et al. | |

(56) References Cited

U.S. PATENT DOCUMENTS

| | | |
|---|---|---|
| 2012/0189711 A1 | 7/2012 | Greenberg et al. |
| 2013/0304020 A1 | 11/2013 | Wilt et al. |
| 2013/0324966 A1* | 12/2013 | Park .................... A61M 1/0056 604/506 |

FOREIGN PATENT DOCUMENTS

| | | | |
|---|---|---|---|
| EP | 0573117 A1 | 8/1998 | |
| EP | 0771570 A1 | 4/2002 | |
| EP | 2005846 A1 * | 12/2008 | ............. A23B 7/158 |
| WO | WO0038756 A1 | 7/2000 | |
| WO | WO2004105838 A3 | 12/2004 | |
| WO | WO2012083412 A1 | 6/2012 | |

OTHER PUBLICATIONS

Dyakowski et al., A Three Dimensional Simulation of Hydrocyclone Behaviour, Second International Conference on CFD in the Minerals and Process Industries, CSIRO, Melbourne, Australia, Dec. 6-8, 1999, pp. 205-210.

Waters, Intraoperative Blood Conservation—Every Cell is Sacred, ITACCS, Summer 2005, pp. 144-148.

Haemonetics, Cell Saver 5+ Autologous Blood Recovery System, printed from internet on Aug. 14, 2013.

Ahmed, Application of Hydrocyclone for Cell Separation in Mammalian Cell Perfusion Cultures, 2005, 150 pages.

Patent Cooperation Treaty, PCT International Search Report, dated Nov. 18, 2013, from PCT Application No. PCT/US2013/054920, 3 pages.

Patent Cooperation Treaty, PCT International Search Report, dated Nov. 18, 2013, from PCT Application No. PCT/US2013/054921, 3 pages.

Ronai et al., "Improving Autologous Blood Harvest: Recovery of Red Cells from Sponges and Suction", Anaesth Intensive Care 1987, 15, pp. 421-424.

* cited by examiner

SYSTEMS AND METHODS FOR BLOOD RECOVERY FROM ABSORBENT SURGICAL MATERIALS

CROSS REFERENCE TO RELATED APPLICATIONS

This application is a divisional of U.S. patent application Ser. No. 13/966,906, filed Aug. 14, 2013, entitled, "SYSTEMS AND METHODS FOR BLOOD RECOVERY FROM ABSORBENT SURGICAL MATERIALS", which claims the benefit of Provisional Patent Application Ser. No. 61/683,315, entitled "SYSTEMS AND METHODS FOR BLOOD RECOVERY FROM ABSORBENT SURGICAL MATERIALS" filed on Aug. 15, 2012, to which priority is claimed pursuant to 35 U.S.C. § 119 and which is hereby incorporated herein by reference in its entirety.

TECHNICAL FIELD

This disclosure relates to systems and methods for recapture of blood cells for autotransfusion during surgical procedures.

BACKGROUND

Autotransfusion is a practice used in a surgical environment in which a person receives their own blood for a transfusion, instead of banked donor blood. This process can reduce the risk of infection from banked blood supplies such as HIV, hepatitis C, cytomegalovirus, bacterial contamination and other transmissible infections and is commonly used in intraoperative and postoperative situations where the use of homologous blood is contraindicated. Transfusion with banked blood supplies can increase the risk of acute or delayed hemolytic reactions, allergic reactions, post-transfusion purpura and transfusion-associated acute lung injury (TRALI). In addition, some patients refuse transfusion with banked blood due to philosophical or religious reasons.

The use of autotransfusion can be particularly beneficial where the patient is at risk of losing one or more units of blood during surgery, in cases involving rare blood types, or where the risk of infectious disease transmission is high.

Certain devices are capable of collecting blood from the surgical field, separating viable red blood cells from plasma, platelets, white cells, anticoagulants, and other substances, and re-introduce the red blood cells into the patient. One such device is produced by Haemonetics Corp. of Braintree, Mass., and sold under the "Cell Saver"™ brand.

SUMMARY

In one exemplary aspect, systems and methods are described for improving salvage of a patient's red blood cells during surgical procedures. In one embodiment, an assembly including a basin is configured to receive blood-soaked absorbent materials used in surgery, e.g., sponges, gauze, and the like; the basin is further configured to collect blood from the absorbent materials safely and efficiently, so that the extracted blood can be transferred to a device that separates red blood cells from the other liquids and substances.

The systems and methods described herein provide certain distinct advantages. One advantage includes the ability to salvage blood cells from absorbent materials used during surgery that might otherwise be discarded. Another advantage includes providing a safe method for extracting blood from absorbent materials used during surgery wherein the risk of transmitting a blood-borne disease to surgical staff is minimized. Another advantage includes providing a system for safely disposing of blood-soaked absorbent materials as an alternative to discarding the materials in a trash basin. Yet another advantage includes improvement in the accuracy of determining patient blood loss during surgery. Other advantages will be apparent to those skilled in the art of surgery and medical devices for salvaging blood.

Unless otherwise defined, all technical and scientific terms used herein have the same meaning as commonly understood by one of ordinary skill in the art. Although methods and materials similar or equivalent to those described herein can be used in the practice or testing of any described embodiment, suitable methods and materials are described below. In addition, the materials, methods, and examples are illustrative only and not intended to be limiting.

The foregoing summary is illustrative only and is not intended to be in any way limiting. In addition to the illustrative aspects, embodiments, and features described above, further aspects, embodiments, and features will become apparent by reference to the drawings and the following detailed description and claims.

DESCRIPTION OF DRAWINGS

The present embodiments are illustrated by way of the figures of the accompanying drawings in which like references indicate similar elements, and in which.

DETAILED DESCRIPTION OF ILLUSTRATIVE EMBODIMENTS

In one exemplary aspect, systems and methods are provided for salvaging a patient's blood cells from blood-soaked absorbent materials used during surgery. In the description that follows, absorbent materials can include, without limitation, sponges, gauze, tape, cloth, felt, or any other material capable of absorbing blood or bodily fluids, including materials made from natural or synthetic fibers, or a blend of both. Two exemplary absorbent materials are Cottonoid™, provided by Codman and Shurtleff, Inc., Raynham, Mass., USA; and Spetzler Neruo Patties, provided by OMT, LLC, Ft. Lauderdale, Fla., USA. Generally, the disclosed systems and methods provide the ability to extract blood from blood-soaked surgical materials and transport the blood to a cell salvage machine such as a Cell Saver™ device.

Figure 1:
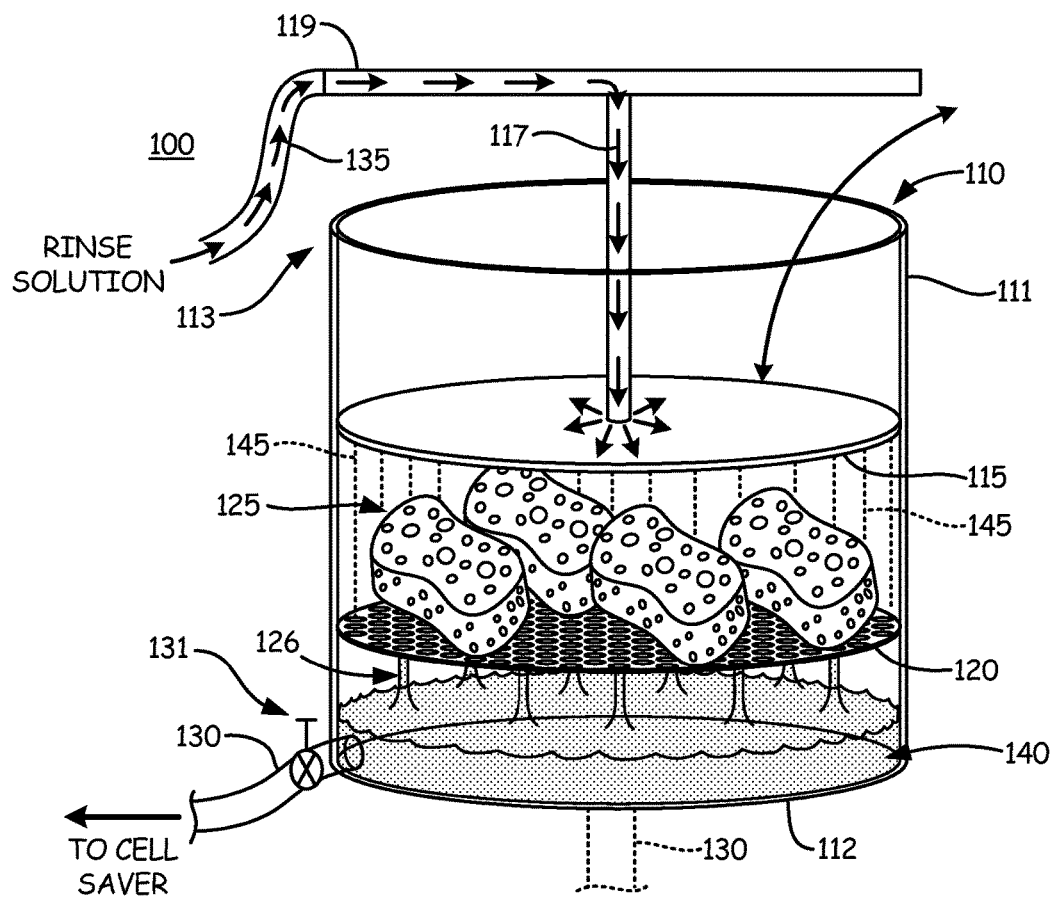
FIG. 1 is a system for extracting blood from an absorbent material, according to one embodiment.

FIG. 1 is a system 100 for extracting blood from an absorbent material, according to one embodiment. The system 100 includes a basin 110 having a fixed, perforated shelf 120 arranged at a height $h_s$ above the basin floor 112. During use, the perforated shelf 120 can support absorbent materials such as the sponges 125 illustrated in FIG. 1. In a preferred embodiment, the perforated shelf 120 can be perforated stainless steel, although other suitable materials can be used, including, but not limited to plastics, aluminum, galvanized steel, or fabrics. In one embodiment, shelf legs can support the perforated shelf 120 above the basin floor 112. (See, e.g., the embodiment of FIG. 2.) In another embodiment, the vertical wall 111 of the basin 110 can include an interior circumferential notch configured to receive and support the perforated shelf 120. In one embodiment, the basin 110 can be formed from two halves that can be disassembled and re-assembled so that components of the system 100 can be washed and sterilized for repeated use.

In this embodiment, the system 100 further includes a plunger plate 115 integral with a vertical handle member 117 which itself is integral with a horizontal handle member 119. The plunger plate 115 can be a solid or porous plate having a diameter substantially equal to, or slightly less than the inner diameter of the basin 110 to allow the plunger plate 115 to be shifted vertically within the basin 110 during use, as described in greater detail below. The plunger plate 115 can be of a desired thickness; however, thinner plates can allow for tilting of the plate 115 within the basin 110, while thicker plates may reduce tilting. The plunger plate 115 can be removed completely from within the basin 110 as illustrated by the double-headed arrow in FIG. 1 so that absorbent materials can be placed in the basin 110 during use.

In this embodiment, during use, blood-soaked materials such as the illustrated sponges 125 can be placed on the perforated shelf 120 within the basin 110. The plunger plate 115 can be applied with a downward shifting force upon the sponges 125 to cause fluids 126 retained therein to be squeezed out and collected in the lower portion 140 of the basin 110.

In this embodiment, a tube 130 is configured to transport the fluid collected in the lower portion 140 of the basin to a cell salvage machine. In one embodiment, this can be accomplished using a vacuum that draws fluid 126 from the lower portion of the basin 140 to the cell salvage machine. In another embodiment, the system 100 can be placed above a cell salvage machine so that any fluids collected in the basin 110 are transported to the cell salvage machine under the influence of gravity. It will be understood that the illustrated placement of the tube 130 in FIG. 1 is one of many options that will be apparent to those skilled in the relevant arts, and that other configurations may provide certain advantages. For example, the tube 130 can be centrally-located beneath the basin 110 in a vertically-oriented manner (shown as a dashed line in FIG. 1 to illustrate one alternative approach). In one embodiment, the bottom portion 140 of the basin can have a conical shape leading to a centrally-located outlet port. (See, e.g., the embodiment of FIG. 2.) Such an alternative construction can be beneficial in collecting a maximum amount of blood and fluids from the basin 110.

In this and other embodiments, the system 100 can be configured to provide rinse solution 145 to the absorbent materials, e.g., the sponges 125 illustrated in FIG. 1. The rinse solution 145 can be applied to the absorbent materials to assist in extracting blood and other fluids alone, or in combination with the application of downward extraction pressure previously described. In the embodiment shown, a rinse solution 145 can be flowed through a tube 135 into the horizontal handle member 119, which, in such an embodiment, would be hollow. The horizontal handle member 119 can be coupled to the vertical handle member 117, also hollow in such an embodiment, to allow the rinse solution 145 to be flowed to the plunger plate 115. The plunger plate can include radially-extending passages or channels that disperse the rinse solution 145 across the surface of the plunger plate 115, and the plunger plate 115 can be configured to evenly disburse the rinse solution 145 to the absorbent materials below, as illustrated in FIG. 1. In one embodiment, the plunger plate 115 can be configured similar to a shower head, where rinse solution 145 can be introduced to the plunger plate 115 via the vertical handle member 117 and then dispersed to produce a shower-like effect as illustrated.

In this embodiment, the system 100 can include a trigger mechanism for controlling the flow of rinse solution 145 by a user. For example, the system 100 can include a thumb switch or lever that allows a user to flow rinse solution on demand. As is known in the art, it can be beneficial when using cell salvaging machines to minimize the amount of rinse solution introduced into the machine. Thus, in one approach, a user can extract a majority of blood and other fluids from the absorbent materials using the downward shifting force previously described, and then apply a small or desired amount of rinse solution to extract remaining blood and other fluids.

In this and other embodiments, the rinse solution can be formulated according to user preference. For example, a rinse solution can be a saline solution. In another example, the rinse solution can include one or more anticoagulants such as citrates, heparin and its derivatives, coumarins, acenocoumarol, phenprocoumon, atromentin, phenindione, among others.

It will be understood that various other substitutions and alternatives can be used to provide the capability of rinsing absorbent materials within the basin 110. For example, a spigot (not shown in FIG. 1) can be integral with, or removably attached to an upper portion (113) of the basin 110 which can be selectively controlled by a user to flow rinse solution over the absorbent materials. In one alternative approach, a syringe can be used.

In this and other embodiments, the system 100 can be configured to allow measurement of collected blood and other fluids from the absorbent materials. An accurate determination of blood loss during surgery can be an important factor in patient care, as is well known in the surgical arts. Thus, in this and other embodiments, the basin 111 can have, for example, graduated markings allowing a user to visualize and measure blood and fluids collected from the absorbent materials. The graduated markings can be placed, e.g., on the side of the basin 110 beginning at the bottom portion (140) of the basin and extending vertically, toward the top portion (113) of the basin 110.

Figure 1A:
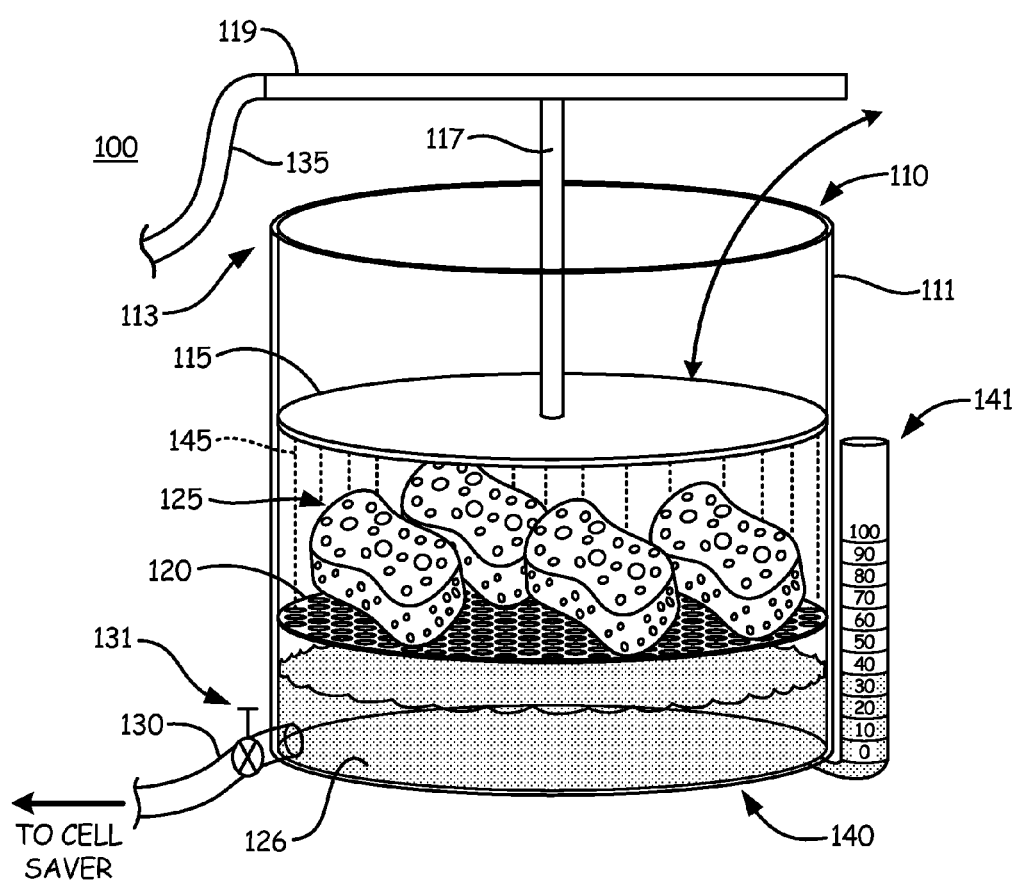
FIG. 1A is a system for extracting blood from an absorbent material according to one embodiment.

Referring now to FIG. 1A, in this and other embodiments, the basin 110 can include an integral measurement tube 141 capable of providing an accurate measurement of collected blood and fluids 145 from the sponges 125. In this embodiment, the measurement tube 141 can have a small inner diameter, e.g., 1 cm, 2 cm, 3 cm, etc., and is in fluid communication with the bottom portion (140) of the basin 110. As blood and other fluids 126 are extracted from the sponges 125 and collected in the bottom portion 140, the blood and other fluids fill the measurement tube 141 accordingly. The measurement tube 141 can include graduated markings to indicate, through appropriate calibration, if necessary, the approximate volume of blood and other fluids 126 collected in the bottom portion 140 of the basin 110. In this example, the measurement tube 141 includes markings for 10, 20, 30, . . . 100 milliliters (mL).

Figure 2:
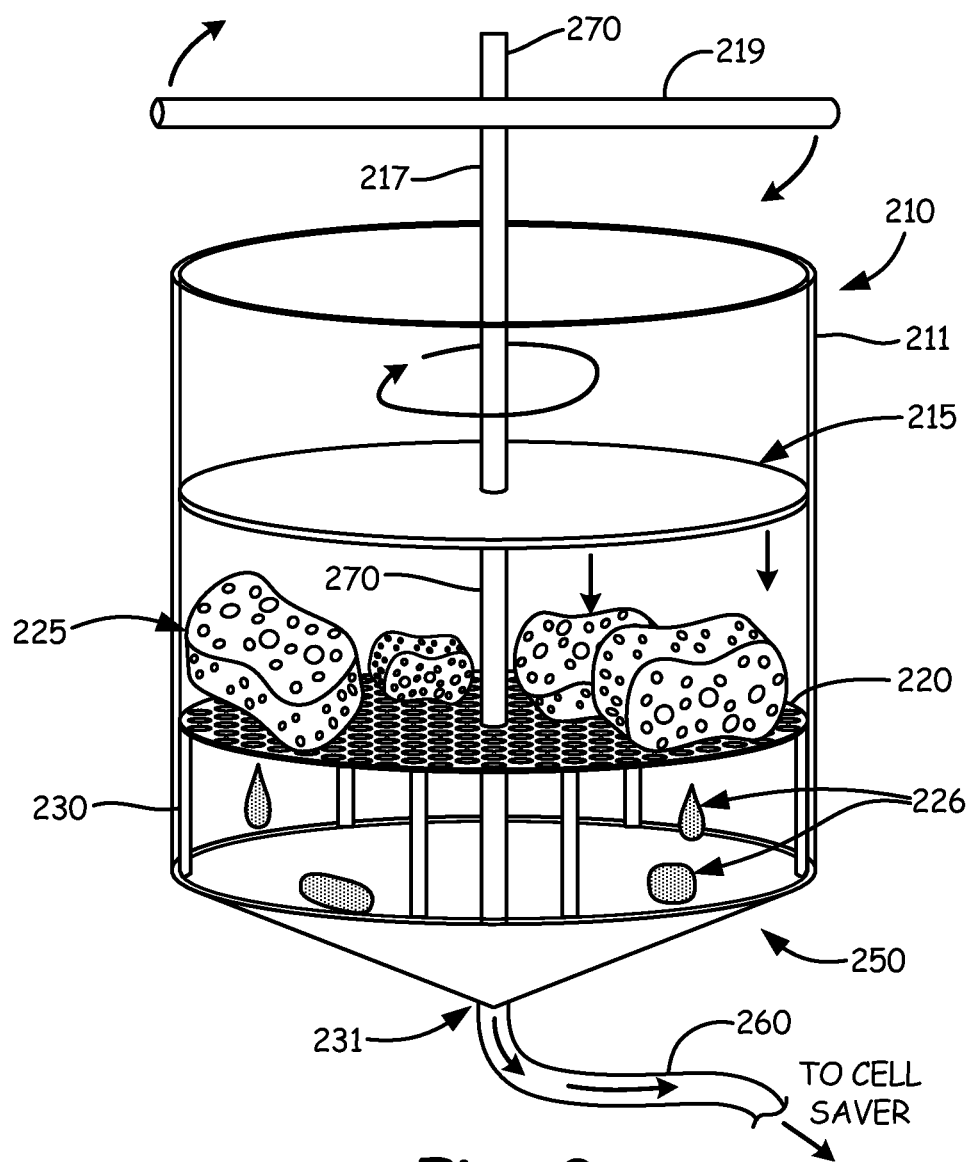
FIG. 2 is a system for extracting blood from an absorbent material according to one embodiment.

Referring now to FIG. 2, a system 200 for extracting blood from an absorbent material is shown, according to one embodiment. Similar to the embodiment illustrated in FIG. 1, the system 200 includes a basin 210 having a conical bottom portion 250, a porous shelf 220, and a plunger plate 215. In this embodiment, the porous shelf 220 is supported vertically above the conical bottom portion 250 by a plurality of triangular-shaped stands 230, although any other method or material can be used for the same or similar purpose. The porous shelf is configured to hold absorbent materials, sponges 225 in this example, containing blood or other bodily fluids, e.g., collected during surgery.

In this embodiment, the basin 210 includes an elongate, exteriorly-threaded rod 270 extending vertically from the apex 231 of the conical bottom portion 250 through the porous shelf 220 as illustrated. The plunger plate 215 includes an aperture located at the origin (i.e., the center of the circular plate). A hollow rod 217 includes matching interior threads and is substantially centered over the aperture of the plunger plate 215 so as to threadingly receive the rod 270. Rotation of handle 219 causes threading of the hollow rod 217 onto the rod 270 and brings the plunger plate 215 into a substantially confronting relationship with the porous shelf 220 to squeeze blood 226 and other fluids from the absorbent materials. In this embodiment, the blood 226 and other fluids are collected by the conical bottom portion 250 and directed under gravitational influence toward an outlet port (not shown in FIG. 2 for clarity). The output port is connected to a tube 260 configured to carry the blood 226 and other fluids to a cell salvaging machine.

In this embodiment, a user can extract blood and other fluids from the absorbent materials, e.g., sponges 225, by placing the absorbent materials upon the porous shelf 220, arranging the plunger plate and hollow rod 217 so that the hollow rod 217 can be threaded onto the rod 270, then turning the handle 219 such that the plunger plate is driven down upon the absorbent materials, squeezing absorbed substances therefrom.

The system 200 can include features of other embodiments described herein. For example, the system 200 can include a rinse feature similar to that described with respect to FIG. 1, to aid in extracting a maximum amount of blood or other absorbed substance within the absorbent materials.

Blood and bodily fluids can be extracted from absorbent materials used during surgery by a variety of methods. For example, absorbent materials can be spun so that absorbed fluids are extracted by centrifugal forces, shaken, vibrated, placed under vacuum, or any other method.

Figure 3:
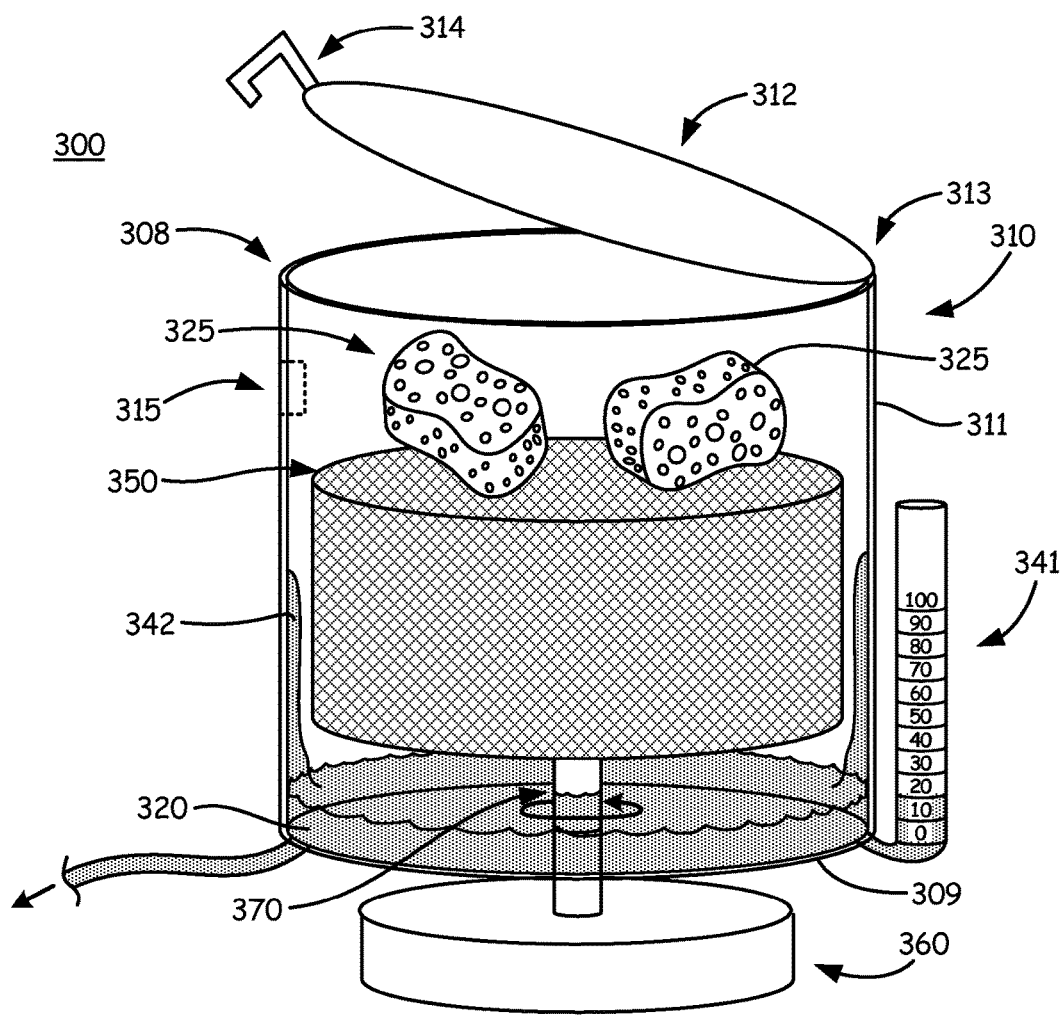
FIG. 3 is a system for extracting blood from an absorbent material according to one embodiment.

Referring now to FIG. 3, a system 300 for extracting blood and other bodily fluids from absorbent surgical materials is shown according to one embodiment. In this embodiment, the system 300 includes a cylindrical basin 310 having a circumferential side wall 311, a floor 309, and a top portion 308 which is open so as to allow absorbent materials, sponges 325 in this example, to be placed within the basin 310.

In this embodiment, the system 300 includes a rotatable basket 350 configured within the basin 310 so as to allow blood and other materials absorbed in absorbent materials to be extracted using centrifugal force. In this embodiment, the rotatable basket 350 includes porous side walls and a porous bottom so that droplets 342 of blood and other materials can escape the basket 350 and collect on the side wall 311 and floor 309 of the basin 310 when the basket is spun. The collected blood 320 can be evacuated from the basin 310 via a tube 352 that, in a preferred embodiment, leads to an inlet port of a cell salvage machine (not shown in FIG. 3).

In this embodiment, the system 300 includes a motor 360, which can be, e.g., a variable-speed electric motor, configured to rotate a shaft 370 that is integral with, or attached to the floor of the basket 350 as illustrated. It will be understood that other configurations and motorized assemblies can be used for the purpose of spinning the basket 350 with sufficient speed to cause blood and other materials within the absorbent materials to be extracted by centrifugal force. Similar to other embodiments, the system further includes a volume gauge 341 for accurately determining the volume of blood and other fluids collected (indicated by the fluid at the bottom of the basin 310, reference numeral 320), which has been described herein.

In this embodiment, the system 300 includes a lid 312 configured to sealingly engage with the upper portion 308 of the basin 310 so as to reduce the likelihood of blood and other substances splashing out or otherwise escaping the basin 310 when the basket 350 is spinning. In this embodiment, the lid 312 is hingedly attached to the side wall 311, allowing the lid to be opened and closed as indicated by the double-headed arrow. The lid 312 further includes a latch member 314 configured to lockingly engage a complimentary recess 315 in the side wall 311 to keep the lid closed when desired, e.g., when the basket is spinning.

As is known in the art, healthy red blood cells can be damaged relatively easily from the effects of applied mechanical force or pressure. Thus, in some embodiments, it can be advantageous to spin the basket 350 at a slow rate to reduce hemolysis. Under normal operating circumstances, however, it is advantageous to re-introduce blood cells harvested from the operating field in a timely manner. To address these issues, the system 300 can be configured so that the basket 350 spins at an appropriate rate to slowly extract blood from absorbent materials used during surgery while minimizing hemolysis. In one embodiment, the lid 312 of the system 300 can include a splash-proof aperture that allows blood-soaked absorbent materials used during surgery to be placed into the basket 350 while the basket continues to spin. For example, the lid 312 can be made of a resiliently flexible polymer or plastic material and include a pattern of slits that allows a portion of the lid to flex outwardly so that sponges, gauze, and other absorbent materials can be passed through the lid without requiring the lid to be opened.

In another example, the lid 312 can include an aperture which can be opened and closed using, e.g., a slidable tab. In a preferred embodiment, the aperture can be positioned on the lid 312 above the center of the basket 350 so that absorbent materials can be introduced into the basket without requiring opening of the lid.

In yet another example, the system 300 can include a resiliently-flexible, or spring-tensioned partition, e.g., a thin, plastic or metal body, positioned between the lid 312 and the basket 350. The partition can reversibly shift between a first position, where the partition is substantially planar-parallel to the lid when closed, thereby blocking blood expelled from the basket from escaping the basin 311, and a second, angled position, that allows absorbent materials to fall into the basket 350. The aforedescribed embodiments and examples can reduce the likelihood of doctors, nurses, and operating room technicians being exposed to blood and are equally applicable to other embodiments described herein.

Temperature control of blood salvaged from absorbent materials using the systems described herein can be achieved by a variety of methods. In one example, the basin (e.g., basin 310) can include a temperature control assembly that includes heating or cooling elements and thermocouples or other sensors for measuring the temperature of collected blood and fluids 320.

In one general aspect, blood cells can be washed from absorbent materials using a wash solution such as heparinized saline, and the blood cells can subsequently be separated from the wash solution using cyclonic action. In general, cyclonic action can cause blood cells to collect or settle at the bottom of a vessel, where they can be collected in a more concentrated form.

Figure 4:
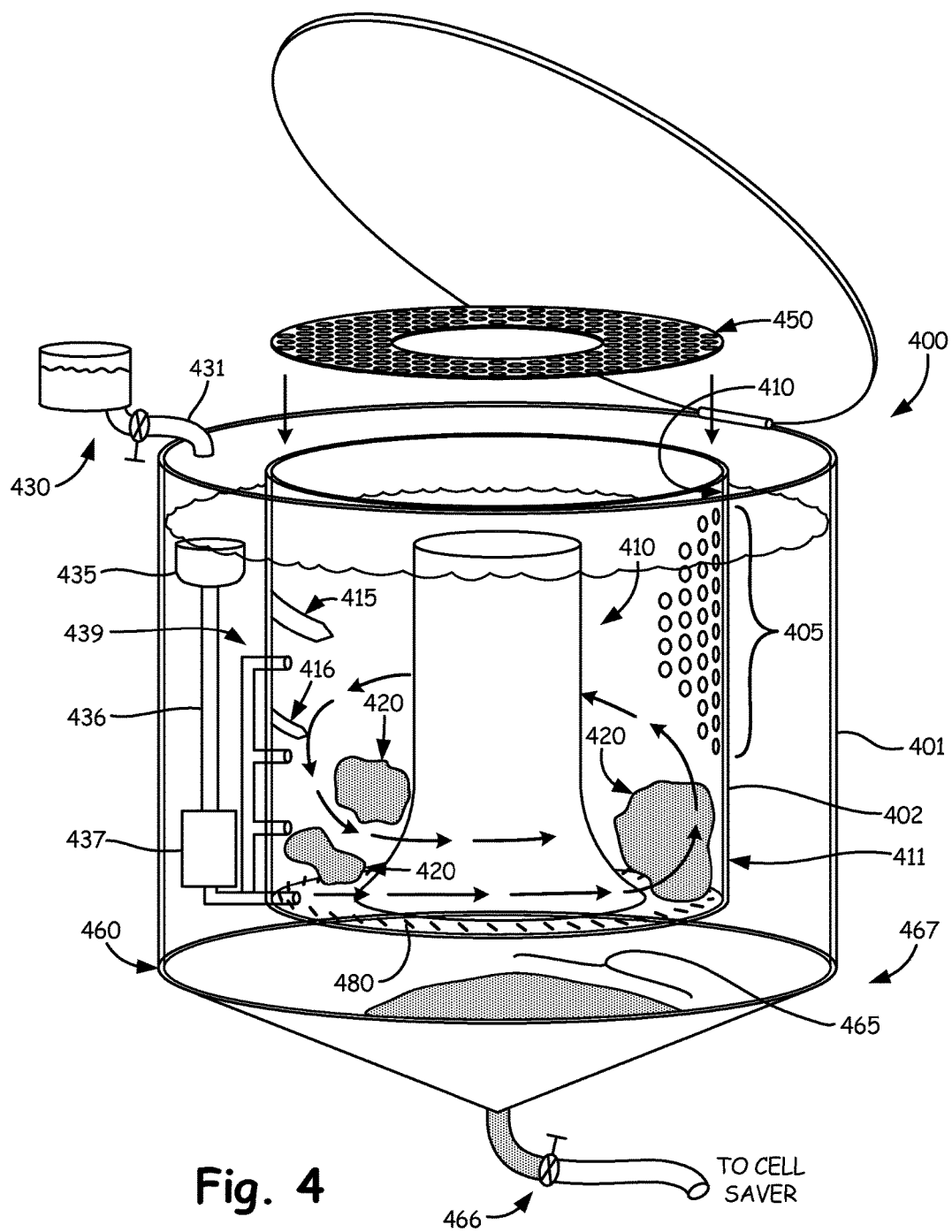
FIG. 4 is a system for extracting blood from an absorbent material using cyclonic action according to one embodiment.

Referring now to FIG. 4, a system 400 for extracting blood and other bodily fluids from absorbent surgical materials using cyclonic action is shown according to one embodiment. In this embodiment, the system 400 includes a first basin 401 capable of at least partially housing a smaller, second basin 402. The second basin 402 can be porous throughout, indicated by the illustrative set of pores 405 (the rest of the pores are not shown in FIG. 4 for clarity). In this embodiment, the system 400 can use cyclonic action of a wash solution to both rinse blood cells from absorbent materials, e.g., sponges 420, and separate blood cells from the rinse solution. In this embodiment, a rinse solution such as heparinized saline solution can be introduced into the first basin 401 or the second basin 402 under pressure and in a substantially horizontal flow direction so as to create a cyclonic vortex of the rinse solution.

In this embodiment, a rinse solution reservoir 430 is configured to fill the first basin 401 via a lumen 431 originating from the reservoir. Fluid pump 437 includes an elongate inlet tube 436 that extends in a generally vertical direction from the pump and terminates with a collection bowl 435 which serves as a fluid intake port for the pump 437. In some embodiments, the collection bowl 435 can be configured so that it floats just under the surface of the rinse solution as illustrated in FIG. 4; this can allow the pump to circulate rinse solution substantially free of blood cells or other substances. In this embodiment, the fluid output of the pump 437 is directed into a multi-output port assembly 439. The assembly 439 is configured to direct the flow of rinse solution in a substantially horizontal direction so as to create cyclonic flow in the first (401) or second (402) basin, or both.

In this embodiment, the second basin 402 includes a cylindrically-shaped pillar 410 configured to assist in creating cyclonic flow of the rinse solution; however, such structure can be omitted in alternative embodiments. In this embodiment, a porous ring 450 having a central aperture can be configured to assist in reducing movement of the absorbent materials during rinsing. The porous ring 450 can have a diameter slightly less than the diameter of the opening of the second basin 402, and an aperture diameter slightly greater than the cross-sectional diameter of the pillar 410, so that the ring 450 can be slidingly placed within the second basin 402. In a preferred embodiment, the ring 450 can slide down the pillar 410 to the bottom portion 411 of the basin to rest upon the absorbent materials (sponges 420 in this example). The pressure of the ring 450 against the absorbent materials can aid in squeezing out blood cells, and additionally keep the absorbent materials from moving about within the cyclonic flow of the rinse solution, when activated. In this embodiment, the floor of the second basin 402 includes pins 480 oriented at an angle into the cyclonic flow direction; the pins 480 can catch on the absorbent materials and further assist in reducing their movement about the basin 402.

In this embodiment, the second basin 402 can include one or more channels, e.g., channels 415, 416 disposed through the wall 410 of the basin that provide a substantially unidirectional exit flow from the second basin 402 into the first basin 401 according to the flow direction of the cyclonic action. Such channels can reduce the likelihood of blood cells re-entering the second basin 402 after being expelled therefrom via cyclonic flow. The termini of the channels 415, 416 where fluids and blood cells enter the solution contained in the first basin 401 can be configured with, e.g., a protruding lip or other structure to further reduce the likelihood of blood cells re-entering the second basin 402.

In this embodiment, the first basin 401 includes an exit port 466 configured to collect blood cells, e.g., the collection of blood cells 465, that settle to the bottom portion 460 of the basin 401. The exit port 466 includes a stopcock 467 configured to allow a user to open and close the exit port 466 as desired.

Still referring to FIG. 4, a method for extracting blood cells from absorbent surgical materials can include the following steps:

First, a user places absorbent materials used during a surgical procedure, and having blood soaked therein, into the second basin 402. The user can optionally place the retaining ring 450 atop the absorbent materials 420 to keep them from moving about the basin during rinsing. The user can then fill the first and second basins 401, 402, respectively with rinse solution from the rinse solution reservoir 430 until the level of the rinse solution is above the collection bowl 435 of the pump 437. The user can then activate the pump 437, which causes rinse solution to be expelled from the multi-output port assembly 439 in a substantially horizontal direction, as illustrated. The rinse solution can flow over and through the absorbent materials to rinse blood cells therefrom, which are then expelled through the pores 405, channels 415, 416, or both, into the first basin 401. The blood cells can settle to the bottom 460 of the first basin 401, where they can be collected via the outlet port 466 and sent to a cell salvage machine.

It will be understood that the configuration of pump 437, including the inlet tube 436, collection bowl 435, and multi-output port assembly 439 as depicted in FIG. 4 is one of many suitable alternatives for providing cyclonic separation of blood cells from rinse solution, and that other configurations can be substituted according to preference or other factors. Similarly, the principle of collecting blood cells using cyclonic action of a rinsing agent can be applied to other embodiments described herein.

A number of illustrative embodiments have been described. Nevertheless, it will be understood that various modifications may be made without departing from the spirit and scope of the various embodiments presented herein. For example, the basins described herein can be composed of any suitable or desirable material, including, but not limited to plastics, glass, metals, etc. In a preferred embodiment, the basin can be formed from resilient Plexiglas to reduce the likelihood of breakage. Various types of motors can be used in embodiments that extract blood from absorbent materials using centrifugal force, including electric and variable-speed electric motors. Substantially cylindrical basins are depicted in the various drawings for simplicity; it will be understood that the basin can be of any desired shape or size to suit the user or provide advantages in manufacturing of the various systems described herein. Similarly, baskets (e.g., basket 350) can be configured or shaped according to preference or manufacturing considerations while still providing the same or similar functionality. It will be understood that the drawings presented herein may not be to scale and that various modifications and improvements can be made without departing from the spirit and scope of their intended use. Accordingly, other embodiments are within the scope of the following claim.

The invention claimed is:

1. An assembly for extracting blood from absorbent material, the assembly comprising;
 a first basin; and
 a second basin configured to be housed at least partially within the first basin and further configured to receive the absorbent material, the second basin having perforated walls;
 wherein the first and second basins are configured to receive a flow of a wash solution and to remove the blood from the absorbent material using a cyclonic flow of the wash solution; and
 wherein a floor of the second basin comprises a plurality of pins that are oriented at an angle into the direction of the cyclonic flow, the pins being configured to catch on the absorbent material to reduce movement of the absorbent material in the direction of the cyclonic flow.

2. The assembly of claim 1, further comprising:
 a fluid pump configured to deliver the wash solution present in the first basin into the second basin to generate the cyclonic flow, wherein the fluid pump is configured to deliver the wash solution in a substantially horizontal flow direction relative to the absorbent material so as to create a cyclonic vortex of the wash solution, and wherein the wash solution comprises a heparinized saline solution introduced into the first basin and/or the second basin under pressure.

3. The assembly of claim 1, wherein the first basin comprises a collection bowl positioned below the wash solution surface, wherein the collection bowl is in fluid communication with the fluid pump to allow for recirculation of wash solution, and wherein a fluid output of the fluid pump is directed into a multi-output port assembly.

4. The assembly of claim 1, wherein the second basin includes a cylindrically-shaped pillar configured to assist in creating the cyclonic flow of the wash solution, and further comprising a porous ring adapted for insertion into the second basin and having a central aperture to allow for insertion of the ring over the pillar.

5. The assembly of claim 1, wherein the second basin has one or more channels disposed through a wall thereof, wherein the one or more channels allow for a substantially unidirectional exit flow from the second basin into the first basin, wherein a terminus of the one or more channels is configured with a structure to further reduce the likelihood of blood cells re-entering the second basin.

6. The assembly of claim 1, wherein a floor of the first basin is concave or conically shaped in order to direct blood to an exit port of the first basin, and wherein a flow regulation device is disposed in the exit port to allow a technician to regulate blood flow from the first basin.

7. The assembly of claim 6, further comprising a cell salvage machine in fluid communication with the exit port of the first basin.

* * * * *